US006245913B1

(12) United States Patent
Singh et al.

(10) Patent No.: US 6,245,913 B1
(45) Date of Patent: Jun. 12, 2001

(54) SYNTHETIC PROCEDURE FOR 5-METHOXY-2-[(4-METHOXY-3,5-DIMETHYL-2-PYRIDINYL)-METHYLTHIO]-IH-BENZIMIDAZOLE HYDROCHLORIDE AND ITS CONVERSION TO OMEPRAZOLE

(75) Inventors: Shiva P. Singh, Gujarat; Siddiqui Mohammed Jaweed Mukarram, Maharashtra; Dilip Ganesh Kulkami, Maharashtra; Manish Purohit, Mahatashtra, all of (IN)

(73) Assignee: Wockhardt Europe Limited, Dublin (IE)

(*) Notice: Subject to any disclaimer, the term of this patent is extended or adjusted under 35 U.S.C. 154(b) by 0 days.

(21) Appl. No.: 09/343,902

(22) Filed: Jun. 30, 1999

(51) Int. Cl.⁷ .................................................. C07D 401/12
(52) U.S. Cl. ................................................ 546/273.7
(58) Field of Search .................................. 546/273.7

(56) References Cited

U.S. PATENT DOCUMENTS

| | | | |
|---|---|---|---|
| 4,045,563 | 8/1977 | Berntsson et al. | 424/263 |
| 4,045,564 | 8/1977 | Berntsson et al. | 424/263 |
| 4,255,431 | 3/1981 | Junggren et al. | 424/263 |
| 4,337,257 | 6/1982 | Junggren et al. | . |
| 4,508,905 | 4/1985 | Junggren et al. | . |
| 4,544,750 | 10/1985 | Brandstrom et al. | 546/290 |
| 4,575,554 | 3/1986 | Sih | 546/271 |
| 4,620,008 | 10/1986 | Brandstrom et al. | 546/271 |
| 4,623,588 | 11/1986 | Nuwayser et al. | . |
| 4,628,098 | 12/1986 | Nohara et al. | 546/271 |
| 4,636,499 | 1/1987 | Brandstrom et al. | . |
| 4,649,043 | 3/1987 | Urquhart et al. | . |
| 4,713,248 | 12/1987 | Kjornes et al. | . |
| 4,725,691 | 2/1988 | Brandstom et al. | . |
| 4,727,150 | 2/1988 | Nohara et al. | 546/271 |
| 4,746,667 | 5/1988 | Carlsson et al. | 514/338 |
| 4,786,505 | 11/1988 | Lovgren et al. | . |
| 4,791,114 | 12/1988 | Constansa et al. | 514/256 |
| 4,800,084 | 1/1989 | Zerbe | . |
| 4,808,413 | 2/1989 | Joshi et al. | . |
| 4,820,521 | 4/1989 | Panoz et al. | . |
| 4,820,522 | 4/1989 | Radebaugh et al. | . |
| 4,853,230 | 8/1989 | Lovgren et al. | . |
| 4,865,849 | 9/1989 | Conte et al. | 424/466 |
| 4,927,640 | 5/1990 | Dahlinder et al. | . |
| 4,963,365 | 10/1990 | Samejima et al. | . |
| 5,026,560 | 6/1991 | Makino et al. | . |
| 5,035,899 | 7/1991 | Saeki et al. | . |
| 5,039,806 | 8/1991 | Brandstram et al. | 546/271 |
| 5,081,154 | 1/1992 | Applegren et al. | . |
| 5,093,200 | 3/1992 | Watanabe et al. | . |
| 5,093,342 | 3/1992 | Tomoi et al. | . |
| 5,096,717 | 3/1992 | Wirth et al. | . |
| 5,102,668 | 4/1992 | Eichel et al. | . |
| 5,106,863 | 4/1992 | Hajos et al. | 514/395 |
| 5,167,964 | 12/1992 | Muhammed et al. | 424/482 |
| 5,186,943 | 2/1993 | Okada et al. | . |
| 5,215,757 | 6/1993 | El-Nokaly | . |
| 5,229,135 | 7/1993 | Philippon et al. | 424/494 |
| 5,232,706 | 8/1993 | Palomo Coll | . |
| 5,275,824 | 1/1994 | Carli et al. | . |
| 5,275,825 | 1/1994 | Okada et al. | . |
| 5,292,522 | 3/1994 | Petereit et al. | . |
| 5,374,730 | 12/1994 | Slemon et al. | 546/271 |
| 5,385,739 | 1/1995 | Debregeas et al. | . |
| 5,391,752 | 2/1995 | Hoerner et al. | . |
| 5,395,626 | 3/1995 | Kotwal et al. | 424/472 |
| 5,399,700 | 3/1995 | Min et al. | . |
| 5,407,686 | 4/1995 | Patel et al. | 424/468 |
| 5,409,709 | 4/1995 | Ozawa et al. | 424/464 |
| 5,422,122 | 6/1995 | Powell | . |
| 5,472,710 | 12/1995 | Klokkers-Bethke et al. | . |
| 5,474,786 | 12/1995 | Kotwal et al. | 424/472 |
| 5,484,608 | 1/1996 | Rudnic et al. | . |
| 5,549,913 | 8/1996 | Colombo et al. | 424/472 |
| 5,593,697 | 1/1997 | Barr et al. | . |
| 5,599,794 | 2/1997 | Eek et al. | . |
| 5,629,305 | 5/1997 | Eek et al. | . |
| 5,633,244 | 5/1997 | Eek et al. | . |
| 5,650,169 | 7/1997 | Conte et al. | 424/472 |
| 5,681,583 | 10/1997 | Conte et al. | 424/472 |
| 5,690,960 | 11/1997 | Bengtsson et al. | . |
| 5,725,880 | 3/1998 | Hirakawa et al. | 424/480 |
| 5,766,623 | 6/1998 | Ayres et al. | . |
| 5,783,212 | 7/1998 | Fassihi et al. | 424/472 |
| 5,783,215 | 7/1998 | Arwidsson et al. | . |
| 5,800,836 | 9/1998 | Morella et al. | 424/489 |
| 5,817,338 | 10/1998 | Bergstrand et al. | . |
| 5,824,341 | 10/1998 | Seth et al. | 424/473 |
| 5,840,329 | 11/1998 | Bai | . |
| 5,840,910 | 11/1998 | Souda et al. | 546/273.7 |
| 5,858,413 | 1/1999 | Jettka et al. | 424/682 |
| 5,885,616 | 3/1999 | Hsiao et al. | 424/472 |
| 5,958,456 | 9/1999 | Baichwal et al. | . |
| 5,958,458 | 9/1999 | Norling et al. | . |
| 6,043,371 | * 3/2000 | Baldwin et al. | 546/301 |

FOREIGN PATENT DOCUMENTS

| | | |
|---|---|---|
| 0005129 | 4/1981 | (EP) . |
| 0240158 | 10/1987 | (EP) . |
| 0268956 | 6/1988 | (EP) . |
| 0277741 | 8/1988 | (EP) . |
| 0277874 | 8/1988 | (EP) . |
| 0302720 | 2/1989 | (EP) . |
| 0305918 | 3/1989 | (EP) . |

(List continued on next page.)

OTHER PUBLICATIONS

CA 127:5362, Nishikubo 1997.*

Primary Examiner—Jane Fan
(74) Attorney, Agent, or Firm—Schwegman, Lundberg, Woessner & Kluth, P.A.

(57) ABSTRACT

The present invention relates to an efficient process for the preparation of 5-methoxy-2-[(4-methoxy-3,5-dimethyl-2-pyridinyl)methylthio]-1-H-benzimidazole hydrochloride starting from 3,5-Lutidine and its conversion to Omeprazole (5-methoxy-2-[(4-methoxy-3,5-dimethyl-2-pyridinyl)methylsulfinyl]-1H-benzimidazole) by selective oxidation with hydrogen peroxide.

20 Claims, No Drawings

FOREIGN PATENT DOCUMENTS

| | | |
|---|---|---|
| 0315414 | 5/1989 | (EP) . |
| 0361874 | 4/1990 | (EP) . |
| 0447168 | 9/1991 | (EP) . |
| 0452862 | 10/1991 | (EP) . |
| 0475536 | 3/1992 | (EP) . |
| 484265 * | 5/1992 | (EP) . |
| 0484265 | 5/1992 | (EP) . |
| 0496437 | 7/1992 | (EP) . |
| 0519144 | 12/1992 | (EP) . |
| 0533264 | 3/1993 | (EP) . |
| 0540147 | 5/1993 | (EP) . |
| WO 98/50361 * | 11/1998 | (EP) . |
| WO 99/10326 * | 3/1999 | (EP) . |
| 540.147 | 2/1985 | (ES) . |
| 2241889 | 9/1991 | (GB) . |
| 85/03436 | 8/1985 | (WO) . |
| 87/02240 | 4/1987 | (WO) . |
| 98/40069 | 9/1998 | (WO) . |
| 98/52564 | 11/1998 | (WO) . |
| 98/53803 | 12/1998 | (WO) . |
| 99/25323 | 5/1999 | (WO) . |

* cited by examiner

SYNTHETIC PROCEDURE FOR 5-METHOXY-2-[(4-METHOXY-3,5-DIMETHYL-2-PYRIDINYL)-METHYLTHIO]-IH-BENZIMIDAZOLE HYDROCHLORIDE AND ITS CONVERSION TO OMEPRAZOLE

BACKGROUND OF THE INVENTION

1. Field of the Invention

This invention relates to synthetic procedures for the manufacture of 1H-benzimidazole intermediates and their conversion to Omeprazole by an efficient and economical oxidation.

2. Background of the Art

Omeprazole (5-methoxy-2-[(4-methoxy-3,5-dimethyl-2-pyridinyl)methylsulfinyl]-1H-benzimidazole) is a known inhibitor of gastric acid secretion and is prescribed for the treatment and prevention of gastrointestinal inflammatory diseases such as gastritis, gastric ulcer and duodenal ulcers. Omeprazole has the following structural formula of 5-methoxy-2-[(4-methoxy-3,5-dimethyl-2-pyridinyl)methysulfinyl]-1H-benzimidazole hydrochloride.

Synthetic preparations of Omeprazole typically involve several steps and utilize either 2,3,5-collidine or 3,5-Lutidine as starting material. U.S. Pat. No. 4,255,431 and U.S. Pat. No. 4,620,008 disclose processes for the synthesis of Omeprazole from 3,5-Lutidine. There 3,5-Lutidine is converted to 2-Chloromethyl-3,5-dimethyl-4-methoxy pyridine hydrochloride which is then coupled with 5,4-methoxy-2-mercaptobenzimidazole followed by oxidation with metachloroperoxy benzoic acid.

European Patent Application No. 484265 A1 describes a synthesis of Omeprazole from 2,3,5-Collidine and involves the oxidation of 5-methoxy-2-[(4-methoxy-3,5-dimethyl-2-pyridinyl)methylsulfinyl]-IH-benzimidazole (II) with meta chloroperoxybenzoic acid or with hydrogen peroxide in the presence of ammonium molybdate,

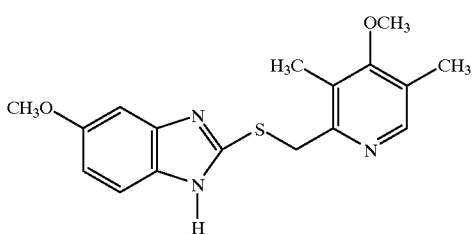

II

Substituted benzimidazoles containing a pyridine radical of the formula II are disclosed, for example, in European patent No. 0005 129. A problem with these compounds is their stability characteristics. Upon storage without any special precautions being taken, they are degraded at a rate which is higher than desired. When Omeprazole (which is a substituted benzimidazole disclosed in this European Patent cited above) is stored at accelerated conditions, that is at 37° C. and at a relative humidity of 80% for a period of 6 months, about 6% of the substance is converted to degradation products.

U.S. Pat. No. 4,620,008 also describes a process for 2-Chloromethyl-3,5-dimethyl-4-methoxy pyridine hydrochloride from 2,3,5-Collidine. U.S. Pat. No. 4,620,008 particularly provides novel compounds which are useful as intermediates in the preparation of therapeutically active compounds such as benzimidazole derivatives which contain a pyridylmethyl radical of the formula II, and methods for the preparation of such compounds of a defined formula I wherein R is H or CH3, are novel and useful intermediates in the preparation of pharmaceutically useful compounds, e.g., substituted benzimidazoles of the general formula I. The compounds of the defined formula are the products obtained from a preceding nitration reaction, for which the N-oxide form may be considered necessary, and the following substitution reaction in which the pyridine N-oxide form is very advantageous considering the yields. In addition, the N-oxide state of the compounds of the defined formula is very advantageous for the subsequent conversion to the 2-hydroxymethylpyridine (procedures A and B). Direct hydroxymethylation of the corresponding non-oxidized pyridines only gives low yields (<20%).

The non-oxidized pyridines may advantageously be prepared by processing both the nitration step and the substitution step without isolation of the intermediate nitropyridine. Furthermore they are stable and can be stored in bulk form. For example, the non-oxidized pyridines are useful as intermediates in the preparation of the corresponding 2-hydroxymethylpyridine and reactive derivatives thereof or a salt thereof, in which an ortho methanol or reactive esterified methanol group is present for the preparation of the ultimate compound, e.g. Omeprazole. The reactive 2-hydroxymethylpyridine intermediate is then reacted in known manner with a benzimidazole derivative, e.g., 5-methoxy-benzimidazole, where after oxidation the reaction process is performed according to standard Omeprazole synthetic techniques. A preferred method described in U.S. Pat. No. 4,620,008 of preparing Omeprazole is to use a non-oxidized pyridine as an intermediate wherein the variable group ortho to the oxygen group is H or $CH_3$.

Several other reagents for the oxidation of this thioether intermediate (11) have been reported and some of them are perbenzoic acid and peracetic acid (EO 240158), hypohalite salts (EP 268956), iodosobenzene, 3-methyl iodosobenzene (ES 540147) and hydrogen peroxide in combination with a vanadium catalyst (EP 302720). EP 533264 describes an oxidation method which uses magnesium monoperoxy phthalate.

There are several problems in oxidation of 5-methoxy-2-[(4methoxy-3,5-dimethyl-2-pyridinyl)methylthio]-IH-benzimidazole (11) with the oxidizing agents mentioned above. The reaction will not proceed to completion in many cases and the yields are low because of degradation or production of a large number of by-products. The reagents are expensive or the process involves the presence of toxic substances like vanadium salts.

SUMMARY OF THE INVENTION

The present invention provides a simple and efficient oxidation process for the preparation of Omeprazole. The oxidation agent employed here is economical and free from toxic components which are associated with other oxidizing agents described in certain other prior art processes.

The process of the present invention may be-described as a process for the preparation of 5-methoxy-2-[(3,5-dimethyl-4-methoxy-2-pyridinyl)methylsulfinyl]-1H-benzimidazole comprising the following steps:

a) oxidizing 3,5-Lutidine to 3,5-Lutidine-N-Oxide by hydrogen peroxide in acetic acid;

b) reducing excess hydrogen peroxide with analdehyde;

c) nitrating 3,5-Lutidine-N-Oxide to give a nitro compound product;

d) isolating the nitro compound product by filtration after neutralization of the nitration reaction mixture with caustic lye in the presence of water sufficient to dissolve the salts of neutralization;

e) reacting the nitro compound with dimethyl sulfate in a first solvent to give a dimethyl sulfate adduct;

f) reacting the dimethyl sulfate adduct with aqueous ammonium persulfate in alcohol to provide an hydroxymethyl compound;

g) reacting the hydroxymethyl compound with $SOCl_2$ to give a chloromethyl compound;

h) coupling the chloromethyl compound with 5-methoxy-2-mercaptobenzimidazole in a dichloromethane with sodium hydroxide or potassium hydroxide in the presence of a phase transfer catalyst to form a coupled product;

i) nucleophilic substitution of $NO_2$ on the 4-position of the coupled product with a methoxy group to form a thioether;

j) conversion of the thioether compound to its hydrochloride salt; and k) oxidizing the thioether hydrochloride salt to Omeprazole; or a process for the preparation of 5-methoxy-2-[(3,5-dimethyl-4-methoxy-2-pyridinyl)methylsulfinyl]-1H-benzimidazole comprising the following steps:

a) oxidizing 3,5-Lutidine to 3,5-Lutidine-N-Oxide by hydrogen peroxide in acetic acid;

b) reducing excess hydrogen peroxide with formaldehyde;

c) nitrating 3,5-Lutidine-N-Oxide to give a nitro compound product;

d) isolating the nitro compound product by filtration after neutralization of the nitration reaction mixture in the presence of water sufficient to dissolve the salts of neutralization;

e) reacting the nitro compound with dimethyl sulfate in a first solvent to give a dimethyl sulfate adduct;

f) reacting the dimethyl sulfate adduct with aqueous ammonium persulfate in alcohol to provide an hydroxymethyl compound;

g) reacting the hydroxymethyl compound with $SOCl_2$ to give a chloromethyl compound;

h) coupling the chloromethyl compound with 5-methoxy-2-mercaptobenzimidazole in a haloalkane with an alkali metal hydroxide or alkaline metal hydroxide in the presence of a phase transfer catalyst to form a coupled product;

i) nucleophilic substitution of $NO_2$ on the 4-position of the coupled product to form a thioether compound;

j) conversion of the thioether compound to its hydrochloride salt; and k) oxidizing the thioether hydrochloride salt to Omeprazole.

DETAILED DESCRIPTION OF THE INVENTION

A disadvantage associated with prior art processes which utilize the thioether 5-methoxy-2-[(4methoxy-3,5-dimethyl-2-pyridinyl)methylthio]-IH-benzimidazole (11) as an intermediate is the physical nature of this compound. Ordinarily, it is an oil and does not solidify readily. It is very difficult to purify 5-methoxy-2-[(4-methoxy-3,5-dimethyl-2-pyridinyl) methylthio]-IH-benzimidazole by the process of recrystallization or precipitation. Thus, impurities remain associated with it which may lead to complications in the oxidation step. Additionally, the Omeprazole obtained from the 5-methoxy-2-[(4-methoxy-3,5-dimethyl-2-pyridinyl) methylthio]-IH-benzimidazole with impurities requires further purification.

It may also be a benefit of the present invention to provide a process for purifying 5-methoxy-2-[(4-methoxy-3,5-dimethyl-2-pyridinyl)methylthio]-IH-benzimidazole by converting it to a hydrochloride salt and then subsequently isolating it, which reduces the load of impurities carried over from earlier stages.

In the present invention Omeprazole is isolated in the final stage from a combination of solvents by filtration. It can be further recrystallized from dichloromethane-ethyl acetate.

The present process for the preparation of Omeprazole (5-methoxy-2-[(4-methoxy-3,5-dimethyl-2-pyridinyl) methylsulfinyl]-1H-benzimidazole) overcomes a number of disadvantages associated with prior art processes. The thioether 5-methoxy-2-[(4methoxy-3,5-dimethyl-2-pyridinyl) methylthio]-IH-benzimidazole (11), which according to prior art processes is difficult to purify and which leads to the formation of impurities which remain associated with Omeprazole, is purified by converting the thioether to its hydrochloride. The hydrochloride salt of the thioether 11 is a solid, easy to handle and is of high purity, 98%. As a result, its oxidation leads to Omeprazole of high purity and substantially free from impurities.

The purified hydrochloride salt (with the hydrochloride associated with the nitrogen of the pyridine ring) of the thioether 5-methoxy-2-[(4methoxy-3,5-dimethyl-2-pyridinyl)methylthio]-IH-benzimidazole (11) is first converted to its free base and oxidized in a novel way with hydrogen peroxide, e.g., in the presence of phthalic anhydride and alkali base in a two phase system comprising water and an organic solvent for the reactants, e.g., dichloromethane. The alkali bases may, solely for purposes of exemplification, include sodium carbonate, potassium carbonate, sodium bicarbonate and potassium bicarbonate, preferably sodium carbonate.

The organic solvent may be any halohydrocarbon, especially one selected from dichloromethane, carbon tetrachloride or 1,2-dichloromethane. The reaction is economically conducted at any convenient temperature, such as from between about −20° C. to 40° C., between about −10° C. to 10° C., and preferably at −5 to 0° C. These temperatures are merely exemplary and are not intended to be limiting in the practice of the present invention.

After the oxidation reaction is over, excess hydrogen peroxide is reduced by washing it with sodium carbonate solution. The organic layer is concentrated and Omeprazole is precipitated by addition of ethyl acetate and isolated by filtration. Recrystalization from dichloromethane-ethyl acetate affords pure Omeprazole.

The advantage of using a mixed solvent lies in that certain impurities like Omeprazole sulfone remain in solution in the mixed solvent and the Omeprazole obtained is of high purity and without any discoloration. According to a speculation, the mechanism of the oxidation reaction is as follows, Sodium monoperoxy phthalic acid is formed in situ by the action of sodium carbonate and hydrogen peroxide on phthalic anhydride and this is the active oxidizing agent. Thus, the active oxidizing agent is prepared in situ and because of its steric bulk it selectively oxidizes the thioether to Omeprazole without any significant over oxidation. The mechanism is only postulated and no claim is being made to it. This in situ generation of the oxidizing agent offers advantage over other oxidizing agents like meta chloroperoxybenzoic acid and magnesium monoperoxyphthalic acid which are comparatively expensive. The factor of toxicity which is associated with the process of oxidation with metal, catalyst like vanadium is also eliminated.

Another aspect of the present invention comprises a process for the preparation of omeprazole which comprises the steps of:

a) treating 5-methoxy-2-[3,5-dimethyl-4-methoxy-2-pyridinyl)-methyl-thio]-1H-benzimidazole (II) or its hydrochloride salt in a solvent, which has been cooled to a temperature of about 0° C. or less, with hydrogen peroxide in the presence of phthalic anhydride and an alkali base; and b) precipitating omeprazole in a mixture of solvents; and isolating omeprazole by filtration.

According to another aspect of the invention, the crude thioether, without purification as the hydrochloride, can also be oxidized in the same manner to give Omeprazole.

The thioether 5-methoxy-2-[(4methoxy-3,5-dimethyl-2-pyridinyl)methylthio]-IH-benzimidazole (11) required for the process of its conversion to the hydrochloride salt and its subsequent oxidation to Omeprazole is prepared from 3,5-Lutidine and the reaction scheme is shown below.

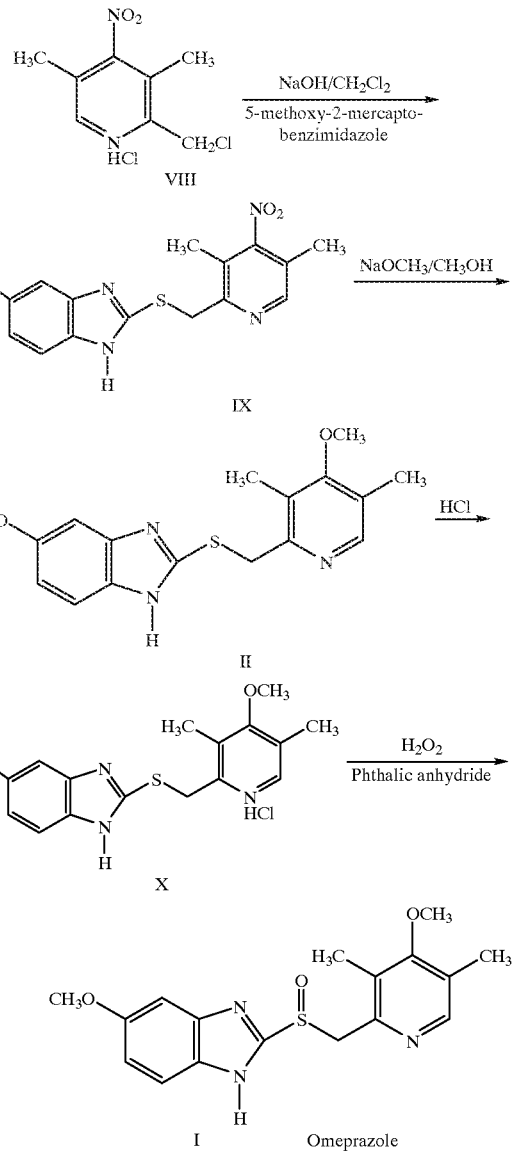

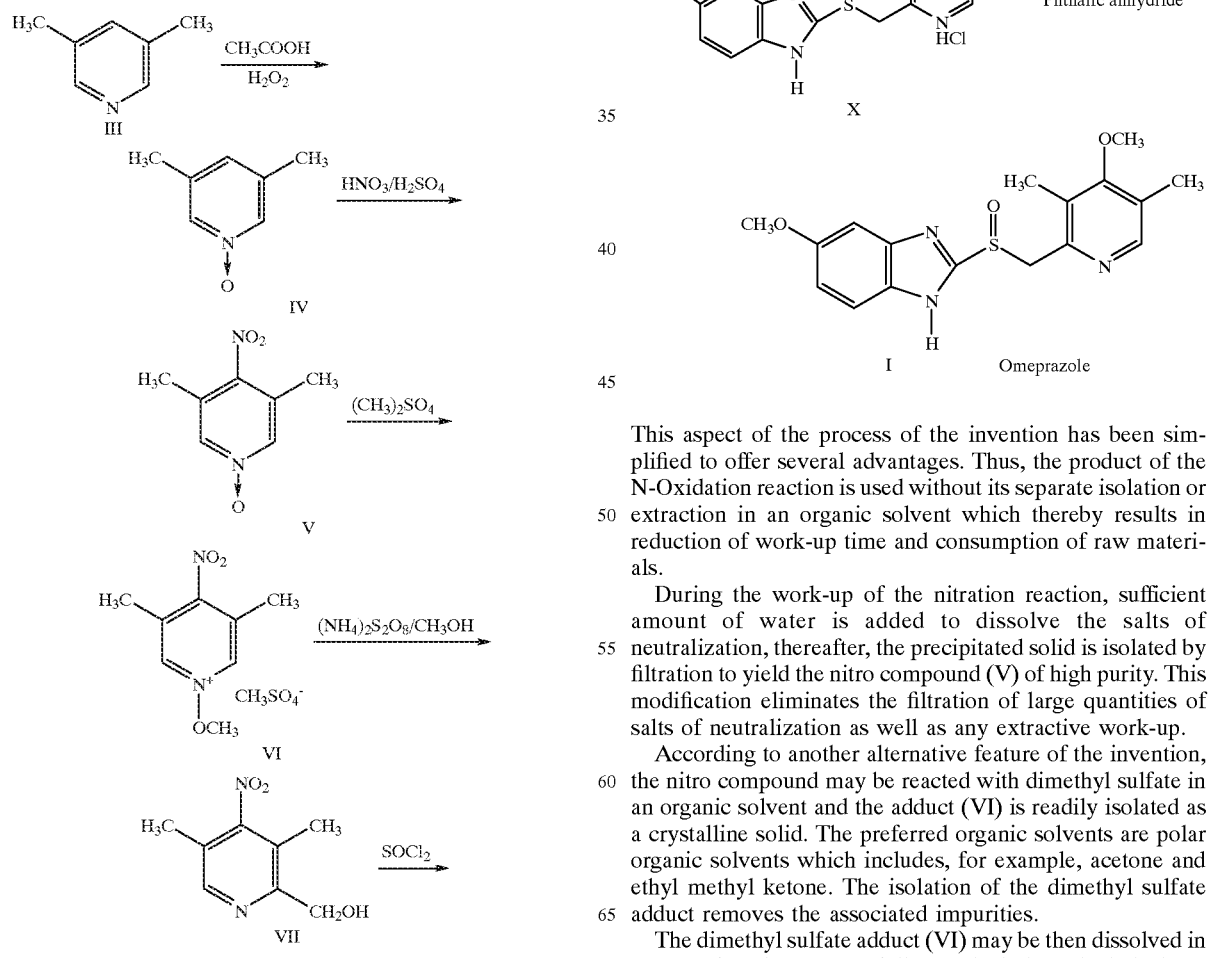

This aspect of the process of the invention has been simplified to offer several advantages. Thus, the product of the N-Oxidation reaction is used without its separate isolation or extraction in an organic solvent which thereby results in reduction of work-up time and consumption of raw materials.

During the work-up of the nitration reaction, sufficient amount of water is added to dissolve the salts of neutralization, thereafter, the precipitated solid is isolated by filtration to yield the nitro compound (V) of high purity. This modification eliminates the filtration of large quantities of salts of neutralization as well as any extractive work-up.

According to another alternative feature of the invention, the nitro compound may be reacted with dimethyl sulfate in an organic solvent and the adduct (VI) is readily isolated as a crystalline solid. The preferred organic solvents are polar organic solvents which includes, for example, acetone and ethyl methyl ketone. The isolation of the dimethyl sulfate adduct removes the associated impurities.

The dimethyl sulfate adduct (VI) may be then dissolved in an organic solvent, especially an alcohol or alcohol plus a cosolvent, such as methanol, and then treated with aqueous ammonium persulfate to yield the hydroxy methyl product (VII).

The hydroxy methyl product may be then converted to the corresponding chloromethyl product by reaction with $SOCl_2$ in an organic solvent, for example, a haloalkane solvent such as dichloromethane. The excess thionyl chloride is destroyed or removed and the chloromethyl product is isolated by filtration. According to another aspect of the invention, the chloromethyl compound (VIII) can be used for the next reaction without its separate isolation.

The chloromethyl compound (VIII) may be then coupled with 5-methoxy-2-mercaptobenzimidazole in a novel method in a two phase system in the presence of sodium hydroxide or potassium hydroxide and a phase transfer catalyst. This offers the advantage of reaction under mild condition and simple work-up where the organic solvent is distilled off and the product (IX) isolated by filtration.

The $NO_2$ group in the coupled product (IX) is then substituted or replaced by a methoxy group ($OCH_3$) by treatment with sodium methoxide in methanol. After work-up, the crude thioether product 5-methoxy-2-[(4methoxy-3,5-dimethyl-2-pyridinyl)methylthio]-IH-benzimidazole (11) is obtained as a solution in the organic solvent (e.g., dichloromethane) which thioether is then purified by converting it to its hydrochloride salt (X). The advantages of this have already been pointed out.

EXAMPLES

In a first step, 3,5-Lutidine (III) is reacted with hydrogen peroxide in acetic acid at 60–90° C. Excess hydrogen peroxide is reduced with an aqueous formaldehyde solution, and acetic acid and water are distilled out under reduced pressure. The distillation residue containing the N-Oxide compound (IV) is used without additional purification for the next reaction.

In a second step, the N-Oxide compound (IV) obtained as above is taken in sulfuric acid and subjected to nitration at 90–100° C. with a nitrating mixture comprising sulfuric acid and nitric acid. After the reaction is over, the reaction mixture is poured over ice and neutralized, for example, with caustic lye (or other alkali or alkaline materials) below 30° C. to a pH of 6 to 7. Water is added to dissolve the salts and the precipitated solid is filtered, washed with water and dried to yield the nitro compound (V) in high purity.

The nitro compound (V) is then treated with dimethyl sulfate in an organic solvent, preferably a polar organic solvent such as acetone (or other ketone, such as ethyl methyl ketone), and product refluxed until a clear solution is obtained. On cooling, a crystalline product separates which is the dimethyl sulfate adduct (VI). The adduct is isolated by filtration.

The dimethyl sulfate adduct (VI) is then converted to the hydroxymethyl compound (VII) by dissolving it in an organic solvent, such as an alcohol, particularly methanol, and treating it at reflux temperature with an aqueous solution of ammonium persulfate. After the reaction is over, the solvent is distilled off, the pH is adjusted to between 8.5 and 11, especially about 10 with a neutralizing material, such as an alkali or alkaline metal oxide or hydroxide, such as caustic lye and the separated hydroxy methyl compound (VII) is extracted in an organic solvent, especially a haloalkane such as dichloromethane.

The dichloromethane solution of the hydroxymethyl compound (VII) is treated at reduced temperatures such as about −20° C. to 30° C., preferably about −10 to 0° C. with $SOCl_2$, after which excess thionyl chloride is destroyed by addition of an alcohol or other active material, especially convenient being methanol, and the solid product is isolated by filtration. Again, these temperatures and conditions are merely examples and are not intended to be limiting on the practice of the present invention. According to another aspect of the invention, the excess thionyl chloride can also be destroyed by addition of alkali or alkaline metal hydroxide solutions such as a sodium hydroxide solution and the resulting dichloromethane solution is used as such for the next coupling reaction.

The chloromethyl compound (VIII) is suspended in an organic solvent, for example only, dichloromethane, 1,2-dichloroethane, carbon tetrachloride, or toluene and reacted with 5-methoxy-2-mercaptobenzimidazole in the presence of aqueous sodium hydroxide(or potassium hydroxide) at 25–40° C. in the presence of a phase transfer catalyst. Phase transfer catalysts are well known in the literature as a class, and include by way of non-limiting examples, triethyl benzyl ammonium chloride, triethyl benzyl ammonium bromide, tetrabutyl ammonium bromide, tetrabutyl ammonium hydrixide, and tetrabutyl ammonium hydrogen sulfate. The organic solvent is distilled off and the product (IX) that separates is filtered off. Again, these temperatures and conditions are merely examples and are not intended to be limiting on the practice of the present invention. According to another aspect of the present invention, the chloromethyl compound (VIII) may be then coupled with 5-methoxy-2-mercaptobenzimidazole without isolating the chloromethyl compound (VIII) and in a manner described above where the chloromethyl compound is isolated separately.

The coupled product (IX) is further reacted with sodium methoxide in an organic solvent such as an alcohol, and especially methanol at 40–60° C. Excess solvent is distilled off and the residue, containing the thioether 5-methoxy-2-[(4-methoxy-3,5-dimethyl-2-pyridinyl)methylthio]-IH-benzimidazole (II), after neutralization and extractive work-up in dichloromethane is treated with HCl gas at 0–40° C. The solid that separates is the hydrochloride salt (X) of the thioether (11) which is isolated by filtration.

In another aspect of the invention the thioether 5-methoxy-2-[(4methoxy-3,5-dimethyl-2-pyridinyl)methylthio]-IH-benzimidazole (11) after extraction into dichloromethane is treated with concentrated HCl at 0–40° C. to yield the hydrochloride salt (X) of the thioether (II).

In a final step, the hydrochloride salt of thioether (II) is converted to the free base by treatment of its suspension in dichloromethane with aqueous sodium hydroxide or potassium hydroxide, and the dichloromethane layer is separated. The oxidation is carried out at reduced temperatures, e.g., about −10 to 10° C. by addition of phthalic anhydride followed by sodium carbonate and hydrogen peroxide. After the reaction is over, the organic phase is separated, washed with aqueous sodium carbonate, dried and concentrated. Addition of ethyl acetate to the concentrated solution of product in dichloromethane results in the crystallization of the Omeprazole, which is isolated by filtration. if necessary, it can be recrystallized from dichloromethane-ethyl acetate.

The invention is further illustrated by reference to the following examples, which are intended to be illustrative and not limiting.

Example 1

3,S-Lutidine-N-Oxide (IV)

Hydrogen peroxide (45%, 200 ml) was added dropwise at 60–70° C. during 2 hours to a mixture of 3, 5-Lutidine (125 gm, 1.16 mole) and acetic acid (400 ml). The mixture was heated to 90° C. and maintained at 90–100° C. for 2 hours after which it was cooled to 60° C. Again hydrogen peroxide (45%, 200 ml) was added dropwise at 60–70° C. during 1 hour and then the mixture was heated to 90° C. and maintained at 90–100° C. for 6 hours. Thereafter, acetic acid and water was distilled off under reduced pressure and the distillation residue obtained was used as a starting product for the nitration reaction.

Example 2

3,5-Dimethyl-4-nitropyridine-N-Oxide (V)

To the distillation residue obtained in Example 1 was added sulphuric acid (146 ml). Thereafter, a nitrating mixture consisting of sulphuric acid (250 ml) and nitric acid (280 ml) was added dropwise during 4 hours at 90–100° C. The reaction mixture was heated further at 90–100° C. for 6 hours, after which it was cooled and poured over crushed ice (4 Kg), Caustic lye (50%, 1150 ml) was added to the yellow solution and the precipitated crystalline compound was filtered under suction. The cake was washed with water and dried in vacuuo oven to yield the product which melted at 171–173° C. Yield 78.5%. A sample crystallized from acetone had a melting point of 174–174.5° C., $^1$H NMR (in CDCl$_3$) 2.33 (s, 6H), 8.04 (s, 2H).

Example 3

3,5-Dimethyl-4-nitropyridine-N-Oxide-dimethyl Sulphate Adduct (VI)

To a suspension of 3,5-Dimethyl-4-nitropyridine-N-Oxide (V) (150 gm, 0.80 mole) in acetone (450 ml) was added dimethyl sulfate (90 ml, 0.95 mole). The mixture was heated to reflux until a clear solution was obtained and then allowed to cool to ambient temperature. An off-white crystalline solid separated out, which was filtered, washed with acetone and dried to yield 220 gm of the adduct. Yield was 83.8% of theoretical.

$^1$H NMR (in D$_2$O) 2.48 (s, 6H), 4.37 (s, 3H), 4.76 (s, 3H), 9.27 (s, 2H).

Example 4

3,5-Dimethyl-2-hydroxymethyl-4-nitropyridine (VII)

3,5-Dimethyl-4-nitropyridine-N-Oxide-dimethyl sulfate adduct (VI) (220 gm, 0.75 mole) was dissolved in methanol (1.0 ltr) and the solution heated to reflux. A solution of ammonium persulfate (140 gm) in water (200 ml) was added dropwise over 4 hours after which reflux was continued for 4 hours. Methanol was distilled off under reduced pressure and the residue was basified to pH 10 by addition of caustic lye (105 ml). The mixture was extracted with dichloromethane (2×400 ml). The dichloromethane layer was dried over sodium sulfate and filtered. The product was used as its solution in dichloromethane for the next reaction.

'H NMR (in CDCl$_3$) 2.16 (s, 3H), 2.31 (S, 3H), 4.43 (t, J=4 Hz, 1H), 4.73 (d, J=4 Hz, 2H), 8.43 (S, 1H).

Example 5

2-Chloromethyl-3,5-dimethyl-4-nitropyridine hydrochloride (VIII)

Method-A

To the cooled dichloromethane solution of product of Example 4 was added thionyl chloride (60 ml, 0.85 mole) dropwise over a period of 2 hours and stirring was continued for a further 2 hours. Methanol (10 ml) was added to destroy excess thionyl chloride and separated product was filtered under suction and washed with dichloromethane. The cake was dried in vacuum oven to yield 55 gm of a cream colored product.

Melting point was 124–126° C.; $^1$H NMR (in CDCl$_3$) 2.58 (s, 3H), 2.67 (s, 3H), 5.19 (s, 2H), 8.52 (s, 1H).

Method-B

Thionyl chloride (60 ml, 0.85 mole) was added dropwise to a cooled solution of 3,5-Dimethyl-2-hydroxymethyl-4-nitropyridine prepared as in Example 4 (from 220 gm of 3,5-Dimethyl-4-nitropyridine-N-Oxide-dimethyl sulfate adduct). After stirring for 2 hours and destroying excess thionyl chloride by addition of methanol, the suspension of 2-chloromethyl-3,5-dimethyl-4-nitropyridine hydrochloride (VIII) in dichloromethane was used as such for the next reaction.

Method-C

To a cooled solution 3,5-Dimethyl-2-hydroxymethyl-4-nitropyridine (prepared as described in Example-4) was added thionyl chloride. The reaction mixture was stirred for 2 hours and then caustic lye (40 ml) was added dropwise with cooling. The resultant mixture was used as such for the next coupling reaction.

Example 6

5-Methoxy-2-[(3,5-dimethyl-4-nitro-2-pyridinyl) methylthio]-1H-benzimidazole (IX)

Method-A

To a suspension of 5-methyl-2-mercaptobenzimidazole (36 gm, 0.2 mole), 2-Chloromethyl-3,5-dimethyl-4-nitropyridine hydrochloride (VII) (47.4 gm, 0.2 mole) and triethyl benzylammonium chloride (5 gm) in a dichloromethane (500 ml) was added dropwise a solution of NaOH (17.6 gm, 0.44 mole) in water (30 ml). The addition was exothermic and the temperature was observed to rise to 40° C. with reflux of dichloromethane—the reaction mixture was stirred for further 6 hours at ambient temperature and filtered. The cake was washed with water and dried in vacuum oven to yield 55.8 gm of cream color product.

Yield 81.1% gm; Melting Point 124–128° C.; $^1$H NMR (in CDCl$_3$), 2.34 (s, 3H), 2.38 (s, 3H), 3.83 (s, 3H) 4.51 (s, 2H), 6.86 (dd, J—9 Hz, 13 Hz, 1H), 7.21 (d, J—13 Hz, 1H), 7.57 (d, J—9 Hz, I H), 8.51 (s, 1H), 11.2 (s, exchange with D$_2$O, 1H).

Method-B

5-Methoxy-2-mercaptobenzimidazole (43 gm, 0.238 mole), and triethyl benzylammonium chloride (5 gm) was added to the product of Example 5 (method-B). To the resultant mixture was added a solution of NaOH (21 gm, 0.525 mole) in water (35 ml). The reaction mixture was allowed to reflux for half an hour after which it was stirred for four hours at ambient temperature. Water (500 ml) was added to the reaction mixture and dichloromethane was distilled at atmospheric pressure. The separated solid was filtered and washed with water to yield 72.00 gm a cream color product. Yield was 87.9% theoretical.

Method-C

To the preparation of Example 5 (method-C) was added 5-methoxy-2-mercapto benzimidazole (43 gm, 0.238 mole) and triethyl benzylammonium chloride (5 gm). This was followed by dropwise addition of solution of sodium hydroxide (10 gm) in water (15 ml). Stirring was continued for 6 hours after which water (500 ml) was added to the reaction mixture and dichloromethane distilled out under atmospheric pressure. The resultant slurry obtained was filtered and the cake washed with water. Drying in vacuum oven yielded the product as cream colored powder (74.5 gm). Yield was 90.9% of theoretical.

Example 7

5-Methoxy-2-[(3,5-dimethyl-4-methoxy-2-pyridinyl) methylthio]-1H-benzimidazole (II)

5-Methoxy-2-[(3,5-dimethyl-4-nitro-2-pyridinyl) methylthio]-1H-benzimidazole (IX) (50 gm, 0.145 mole) was dissolved in methanol and heated to 45° C. A solution of sodium methoxide (50 gm, 0.925 mole) in methanol (150 ml) was added dropwise over a period of 3 hours at 45–60° C. Stirring was continued for another 2 hours and then methanol was distilled off under reduced pressure. To the cooled residue was added water (200 ml) followed by concentrated HCl (65 ml) until the pH of the mixture was 7.5. The reaction mixture was extracted with dichloromethane and the dichloromethane layer was washed with water (2×100 ml). The dichloromethane layer was dried over sodium sulfate and concentrated to yield the product as an amber color syrup. Yield was 40.1 gm, about 83.8% of theoretical. A solid sample was obtained by trituration of the syrup several times with petroleum ether.

Melting point was 87–90° C.

Example 8

5-Methoxy-2-[(3,5-dimethyl-4-methoxy-2-pyridinyl) methylthio]-1H-benzimidazole Hydrochloride (X)

Method-A

HCl gas was bubbled into a cooled solution of 5-Methoxy-2-[(3,5-dimethyl-4-methoxy-2-pyridinyl) methylthiol]-1H-benzimidazole(li) (50 gm) in dichloromethane (250 ml) until no more precipitation was observed. The reaction mixture was warmed to 40° C. and again cooled to 10° C. The solid was filtered under suction and washed with dichloromethane to yield the product (49 gm) as a cream colored fine granular solid. Yield was 88.2%. Melting point 144–148° C. of theoretical Method-B Concentrated HCl (16 ml, 0.16 mole) was added to a solution of 5-methoxy-2[(3,5-dimethyl-4-methoxy-2-pyridinyl)methylthio]-1H-benzimidazole (50 gm, 0.15 mole) in dichloromethane (DCM, 250 ml) and the mixture was heated to reflux. Water was removed by azeotropic distillation and the separated solid was filtered, washed with dichloromethane and dried to yield 45.1 gm of solid. Yield was 81.4% of theoretical.

Example 9

Omeprazole from 5-Methoxy-2-[(3,5-dimethyl-4-methoxy-2-pyridinyl)methylthiol]-1H-benzimidazole To a solution of 5-methoxy-2-[(3,5-dimethyl-4-methoxy-2-pyridinyl)methylthio]-1H-benzimidazole (11) (32.9 gm, 0.1 mole) in dichloromethane (200 ml) was added phthalic anhydride (20 gm, 0.135 mole) and cooled in an ice salt bath. This was followed by addition of sodium carbonate (18 gm, 0.17 mole) and water (20 ml). Hydrogen peroxide (12 ml, 45%, 0.16 mm mole) was added dropwise at −5 to 0° C. and the reaction mixture was stirred at the same temperature. When the reaction was complete as indicated by TLC, water (200 ml) was added, cooling bath was removed and the reaction mixture was stirred for 10 mins. The organic layer was separated and washed with 5% sodium carbonate solution. The separated dichloromethane solution was charcolised and filtered through celite. The filtrate was concentrated to 100 ml and ethyl acetate 100 ml was added thereto. The separated solid was filtered, washed with ethyl acetate and dried in vacuum oven to yield 28.20 gm of Omeprazole. Yield 82.4% of theoretical. Melting Point was 158–160° C. (dec.)

Example 10

Omeprazole from 5-Methoxy-2-[(3,5-dimethyl-4-methoxy-2-pyridinyl)methylthio]-1H-benzimidazole Hydrochloride Sodium hydroxide solution (5%, 100 ml) was added to a suspension of 36.50 gm of 5-methoxy-2-[(3,5-dimethyl-4-methoxy-2-pyridinyl)methylthio]-1H-benzimidazole hydrochloride (X) in DCM (200 ml) and stirred for 10 mins. The DCM (dichloromethane) layer was separated and to it was added phthalic anhydride (20 gm, 0.135 mole). The reaction mixture was cooled and to it was added sodium carbonate (18 gm) and water 20 ml. Hydrogen peroxide (45%, 12 ml) was added dropwise at −5 to 0° C. when the reaction was complete it was worked-up as in Example-9 to yield 29.4 gm of Omeprazole. Yield 85.90%.

What is claimed is:

1. A process for the preparation of 5-methoxy-2-[(3,5-dimethyl-4-methoxy-2-pyridinyl)methylsulfinyl]-1H-benzimidazole comprising the following steps:

a) oxidizing 3,5-Lutidine to 3,5-Lutidine-N-Oxide by hydrogen peroxide in acetic acid;

b) reducing excess hydrogen peroxide with formaldehyde;

c) nitrating 3,5-Lutidine-N-Oxide to give a nitro compound product;

d) isolating the nitro compound product by filtration after neutralization of the nitration reaction mixture in the presence of water sufficient to dissolve the salts of neutralization;

e) reacting the nitro compound with dimethyl sulfate in a first solvent to give a dimethyl sulfate adduct;

f) reacting the dimethyl sulfate adduct with aqueous ammonium persulfate in alcohol to provide an hydroxymethyl compound;

g) reacting the hydroxymethyl compound with $SOCl_2$ to give a chloromethyl compound;

h) coupling the chloromethyl compound with 5-methoxy-2-mercaptobenzimidazole in a haloalkane with an alkali metal hydroxide or alkaline metal hydroxide in the presence of a phase transfer catalyst to form a coupled product;

i) nucleophilic substitution of $NO_2$ on the 4-position of the coupled product to form a thioether compound;

j) treating the thio ether or its hydrochloride salt in a solvent, cooled to a temperature of about 0 C. or less, with hydrogen peroxide in the presence of phthalic anhydride and an alkali base.

2. The process of claim 1 wherein step h) is performed in the presence of a phase transfer catalyst, sodium hydroxide as the alkali metal hydroxide, and dichloromethane as the haloalkane.

3. The process of claim 1 wherein said thioether hydrochloride is converted to a free base before the thioether is converted to Omeprazole.

4. A process for the preparation of Omeprazole which comprises:

treating 5-methoxy-2-[3,5-dimethyl-4-methoxy-2-pyridinyl)-methyl-thio]-1H-benzimidazole (II) or its hydrochloride salt in a solvent, cooled to a temperature of about 0° C. or less, with hydrogen peroxide in the presence of phthalic anhydride and an alkali base.

5. The process of claim 1 wherein said nitrating 3,5-Lutidine-N-Oxide to give a nitro compound is performed without its separate isolation or extraction in an organic solvent.

6. The process of claim 1 wherein isolation of said nitro compound product is followed by neutralization of the reaction mixture.

7. The process of claim 6 wherein neutralization is effected with caustic lye .

8. The process of claim 1 wherein said conversion of the thioether compound to its hydrochloride salt is effected with HCl gas or aqueous HCl solution.

9. The process of claim 4 wherein the solvent comprises at least one solvent selected from the group consisting of dichloromethane, 1,2-dichloroethane, carbon tetrachloride and toluene.

10. The process of claim 4 wherein said alkali base is selected from the group consisting of sodium carbonate, sodium bicarbonate, potassium carbonate, and potassium bicarbonate.

11. The process of claim 4 wherein from about 1 to 2 equivalent of hydrogen peroxide is used per equivalent of 5-methoxy-2-[3,5-dimethyl-4-methoxy-2-pyridinyl)-methyl-thio]-1H-benzimidazole or its hydrochloride salt.

12. The process of claim 4 wherein about 1 to 2 equivalent of phthalic anhydride is used per equivalent of 5-methoxy-2-[3,5-dimethyl-4-methoxy-2-pyridinyl)-methylthio]-1H-benzimidazole or its hydrochloride salt.

13. The process of claim 4 wherein about 1 to 3 equivalent of alkali base is used per equivalent of 5-methoxy-2-[3,5-dimethyl-4-methoxy-2-pyridinyl)-methyl-thio]-1H-benzimidazole or its hydrochloride salt.

14. The process of claim 2 wherein said combination of solvents comprises a combination of both dichloromethane and ethyl acetate.

15. The process of claim 1, wherein the nitro compound product is converted to a dimethyl sulfate adduct.

16. The process of claim 15 wherein said dimethyl sulfate adduct is formed by treating the nitro compound product with dimethyl sulfate in acetone and the resulting adduct is isolated by filtration.

17. The process of claim 1, wherein step h) is performed in the presence of a phase transfer catalyst.

18. The process of claim 14 wherein said phase transfer catalyst is selected from the group consisting of triethyl benzyl ammonium chloride, triethyl benzyl ammonium bromide, tetrabutyl ammonium bromide, tetrabutyl ammonium hydroxide, and tetrabutyl ammonium hydrogen sulfate.

19. The process of claim 6 wherein the first solvent comprises a solvent selected from the group consisting of dichloromethane, 1,2-dichloromethane and carbon tetrachloride.

20. A process for the preparation of 5-methoxy-2-[(3,5-dimethyl-4-methoxy-2-pyridinyl)methylsulfinyl]-1H-benzimidazole comprising the following steps:

a) oxidizing 3,5-Lutidine to 3,5-Lutidine-N-Oxide by hydrogen peroxide in acetic acid;

b) reducing excess hydrogen peroxide with an aldehyde;

c) nitrating 3,5-Lutidine-N-Oxide to give a nitro compound product;

d) isolating the nitro compound product by filtration after neutralization of the nitration reaction mixture with caustic lye in the presence of water sufficient to dissolve the salts of neutralization;

e) reacting the nitro compound with dimethyl sulfate in a first solvent to give a dimethyl sulfate adduct;

f) reacting the dimethyl sulfate adduct with aqueous ammonium persulfate in alcohol to provide an hydroxymethyl compound;

g) reacting the hydroxymethyl compound with $SOCl_2$ to give a chloromethyl compound;

h) coupling the chloromethyl compound with 5-methoxy-2-mercaptobenzimidazole in a dichloromethane with sodium hydroxide or potassium hydroxide in the presence of a phase transfer catalyst to form a coupled product;

i) nucleophilic substitution of $NO_2$ on the 4-position of the coupled product with a methoxy group to form a thioether;

j) treating the thio ether or its hydrochloride salt in a solvent, cooled to a temperature of about 0 C. or less, with hydrogen peroxide in the presence of phthalic anhydride and an alkali base.

* * * * *

UNITED STATES PATENT AND TRADEMARK OFFICE
CERTIFICATE OF CORRECTION

PATENT NO.     : 6,245,913 B1
DATED          : June 12, 2001
INVENTOR(S)    : Shiva P. Singh, Siddiqui Mohammed Jaweed Mukarram, Dilip Ganesh Kulkarni, Manish Purohit It is certified that error appears in the above-identified patent and that said Letters Patent is hereby corrected as shown below:

Title page,
Item [75], under "Inventors", delete "Kulkami" and insert -- Kulkarni --, therefor.

Column 2,
Line 57, delete "be-described" and insert -- be described --, therefor.
Line 63, delete "analdehyde" and insert -- an aldehyde --, therefor.

Signed and Sealed this

Eleventh Day of December, 2001

Attest:

NICHOLAS P. GODICI
Attesting Officer    Acting Director of the United States Patent and Trademark Office